(12) United States Patent
Hausheer et al.

(10) Patent No.: US 7,829,540 B2
(45) Date of Patent: Nov. 9, 2010

(54) COMPOUNDS AND METHODS FOR REDUCING UNDESIRED TOXICITY OF CHEMOTHERAPEUTIC AGENTS

(75) Inventors: Frederick H. Hausheer, Boerne, TX (US); Harry Kochat, San Antonio, TX (US); Qiuli Huang, San Antonio, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 533 days.

(21) Appl. No.: 11/985,244

(22) Filed: Nov. 14, 2007

(65) Prior Publication Data

US 2008/0161603 A1    Jul. 3, 2008

Related U.S. Application Data

(62) Division of application No. 10/843,930, filed on May 12, 2004, now abandoned.

(51) Int. Cl.
*A61K 38/05* (2006.01)
(52) U.S. Cl. ........................................................ 514/19
(58) Field of Classification Search .................. None
See application file for complete search history.

(56) References Cited

OTHER PUBLICATIONS

A Rajca and M Wiessler. Tetrahedron Letters (1990) 31(42), pp. 6075-6076.*

\* cited by examiner

*Primary Examiner*—Andrew D Kosar
(74) *Attorney, Agent, or Firm*—Scott A. Whitaker

(57) ABSTRACT

Novel compositions and formulations are disclosed that have use as toxicity-reducing agents for various chemotherapeutic agents and as treatment for certain diseases and conditions. The compositions of matter are amino acid and peptide heteroconjugated disulfides of 2-mercaptoethane sulfonate sodium.

1 Claim, 2 Drawing Sheets

COMPOUNDS AND METHODS FOR REDUCING UNDESIRED TOXICITY OF CHEMOTHERAPEUTIC AGENTS

RELATED APPLICATIONS

The present patent application is a Divisional Application of U.S. patent application Ser. No. 10/843,930, filed on May 12, 2004 now abandoned and entitled "COMPOUNDS AND METHODS FOR REDUCING UNDESIRED TOXICITY OF CHEMOTHERAPEUTIC AGENTS".

FIELD OF THE INVENTION

The present invention relates to novel compositions of matter, namely certain short-chain peptides, and short chain peptides conjugated with a thioalkane sulfonate or phosphonate salt. The compositions, when administered to patients also receiving chemotherapy for cancer or other diseases, are useful as protective agents to mitigate or eliminate the undesired toxic effects of the chemotherapeutic agent.

BACKGROUND OF THE INVENTION

Since the discovery of the antineoplastic properties of the nitrogen mustards more than 50 years ago, cancer chemotherapy has been an expanding area of scientific endeavor, and has been a critical component of cancer treatment along with surgery and radiation therapy. Where chemotherapy was once accepted only as a means to extend survival time for those patients diagnosed as incurable by surgery and/or radiation therapy, it is now a recognized modality of treatment in nearly all of the more than two thousand variations of cancer.

Modern cancer chemotherapy typically involves a combination of two or three different drugs, and the advances in technology and medical knowledge have greatly improved a patient's chances of recovery in many forms of cancer. The role of antineoplastic agents in cancer therapy varies widely depending upon the form of cancer. For example, chemotherapy is often the primary course of therapy in cancers of the ovary, testis, breast, bladder, and others, in leukemias and lymphomas, and is generally employed in combination with radiation therapy in the treatment of a large number of sarcomas, melanomas, myelomas, and others. In contrast, chemotherapy is often used only as a last resort or as a palliative treatment for most solid tumors, such as carcinomas of the pancreas and lung. There are exceptions within each class of tumor or other neoplasm.

Chemotherapeutic agents, which are commonly referred to throughout this specification as "antineoplastic agents" are classified into a number of diverse groups. The vast majority of these agents act as cytotoxic drugs, and each member of a specific group is postulated to typically exert its cytotoxic effects through a similar biological mechanism. However, it is important to note that a complete understanding of the biological and biochemical mechanisms of action of antineoplastic drugs is not fully known. The mechanisms of action recited in this specification are based upon the current state of the art, and each of these postulated mechanisms may or may not be important to the mechanism of actual cytotoxicity of the drug, or the manner in which the protective agents allay the toxic incidences recited herein.

Unfortunately, nearly all of the antineoplastic agents in use today have the potential to produce significant toxic effects on normal healthy cells apart from the desired killing effects on cancer cells. Drug toxicity can be severe enough to create life-threatening situations, which requires the coadministration of other drugs, the reduction and/or discontinuation of the antineoplastic drug, or the performance of other prophylactic maneuvers, any of which may impact negatively on the patient's treatment and/or the quality of life. Many times, the failure to achieve control of a patient's disease is due to the measures that must be taken to reduce the unwanted toxicity of the antineoplastic agent on healthy cells.

As of January 2003, more than eighty commercial antineoplastic agents have been approved for use in the United States. Even more antineoplastic agents are approved for usage overseas. There are also over two hundred investigational new drugs which are undergoing evaluation as antineoplastic agents in clinical trials in the United States and overseas. In addition, thousands of newly discovered compounds are evaluated every year as potential antineoplastic agents.

Mesna (Sodium 2-mercaptoethane sulfonate; Mesnex®) is an internationally approved drug for use in conjunction with ifosfamide, to reduce the bladder toxicity commonly associated with therewith. The mechanism of action of mesna has been postulated to be its ability to react with acrolein, a metabolite of ifosfamide. Previous teachings taught that mesna was auto-oxidized in the mildly basic environment of blood plasma, and was reduced back to mesna in the acidic environment present in the kidneys and bladder.

Our investigations into the pharmacokinetics of mesna suggest that, in the human bloodstream, mesna reacts with various mercapto-containing amino acids, such as cysteine, homocysteine and glutathione to form disulfides of a heteroconjugate variety. Previously, disulfides of mesna, both the homoconjugate and the disulfide heteroconjugates were thought to be inactive, and that reduction to mesna was required for the drug to work.

Contrary to the prior teachings that suggested its inactive nature, BNP7787 (Disodium 2,2'-dithiobis ethane sulfonate; Tavocept™), the homoconjugated disulfide of mesna, is currently in late-stage human clinical trials in the United States, Europe and Japan as a toxicity-reducing agent when used in conjunction with cisplatin, carboplatin, paclitaxel, and combination regimens thereof. BNP7787 has also been disclosed in a number of United States and international patents as an effective toxicity-reducing agent for a number of other chemotherapeutic drugs.

SUMMARY OF THE INVENTION

The present invention discloses compounds that are heteroconjugates of mesna, which are useful as toxicity-reducing agents when used in combination with various chemotherapeutic agents. The compounds possess the following Formula I: (I) X—S—S—$R_1$-$R_2$, wherein:

$R_1$ is lower alkylene, optionally substituted by aryl, hydroxy, alkoxy, aryloxy, mercapto, alkylthio or arylthio for a corresponding hydrogen atom;

$R_2$ is sulfonate or phosphonate;

X is a sulfur-containing amino acid or a peptide consisting of 2-10 amino acids, optionally substituted by lower alkyl, lower alkenyl, lower alkynyl, aryl, alkoxy, aryloxy, mercapto, alkylthio or hydroxy for a corresponding hydrogen atom; and pharmaceutically acceptable salts and prodrugs thereof.

The present invention also provides for pharmaceutical formulations containing a Formula I compound as the active agent, combined with one or more pharmaceutically acceptable excipients, fillers, diluents or additives to form a pharmaceutically elegant formulation suitable for administration to human patients.

The present invention also provides for methods of reducing the toxicity of treatment regimens that include administration of one or more chemotherapeutic agents. The methods of use involve administering an effective, or toxicity-reducing amount of Formula I compound to a patient undergoing chemotherapy for cancer or other disease.

It is a principle object of the present to provide for novel and useful compounds that reduce or eliminate the undesirable toxicities associated with chemotherapy treatments.

Another object is to provide for pharmaceutical formulations of the novel compounds that may be administered safely and efficiently.

Yet another object is to provide methods for reducing or eliminating the undesirable toxicities commonly associated with chemotherapy.

Various additional objects will become apparent upon a reading of the following description and claims.

DESCRIPTION OF THE PREFERRED EMBODIMENTS

The preferred embodiments herein described are not intended to be exhaustive or to limit the invention to the precise form disclosed. They are chosen and described to explain the principles of the invention, and its application and practical use to thereby enable others skilled in the art to follow its teachings.

Definitions

"Lower alkylene" means a bridging moiety formed of one to six '—$CH_2$—' groups.

"Aryl" means an aromatic ring or ring system consisting of one or more rings, preferably one to three rings, fused or unfused, with the ring atoms consisting entirely of carbon atoms.

"Lower alkyl" means a straight or branched-chain aliphatic hydrocarbon containing one to six carbon atoms.

"Lower alkenyl" and "lower alkynyl" means a straight or branched chain hydrocarbon containing one to six carbon atoms, and with at least one double bond (alkenyl) or triple bond (alkynyl) between two of the carbon atoms.

The present invention comprises novel compounds having the formula: (I) X—S—S—$R_1$-$R_2$, wherein:

$R_1$ is lower alkylene, optionally substituted by aryl, hydroxy, alkoxy, aryloxy, mercapto, alkylthio or arylthio for a corresponding hydrogen atom;

$R_2$ is sulfonate or phosphonate;

X is a sulfur-containing amino acid or a peptide consisting of 2-10 amino acids, optionally substituted by lower alkyl, lower alkenyl, lower alkynyl, aryl, alkoxy, aryloxy, mercapto, alkylthio or hydroxy for a corresponding hydrogen atom; and pharmaceutically acceptable salts and prodrugs thereof.

The present invention also comprises pharmaceutical formulations that include a Formula I compound as active ingredient, and one or more pharmaceutically acceptable excipients, diluents, additives, fillers, etc., wherein the formulation is adapted for administration to mammalian patients.

The present invention also includes methods of reducing the toxicity of various antineoplastic and other drugs by administering effective amounts of the Formula I compound (or a formulation thereof) to the patient in conjunction with the antineoplastic drug.

The Formula I compounds are heteroconjugated disulfides of mesna (2-mercaptoethane sulfonate sodium). The preferred method of synthesizing a Formula I compound is shown in FIG. 1 (Scheme 1) and FIG. 2 (Scheme 2).

Figure 1:
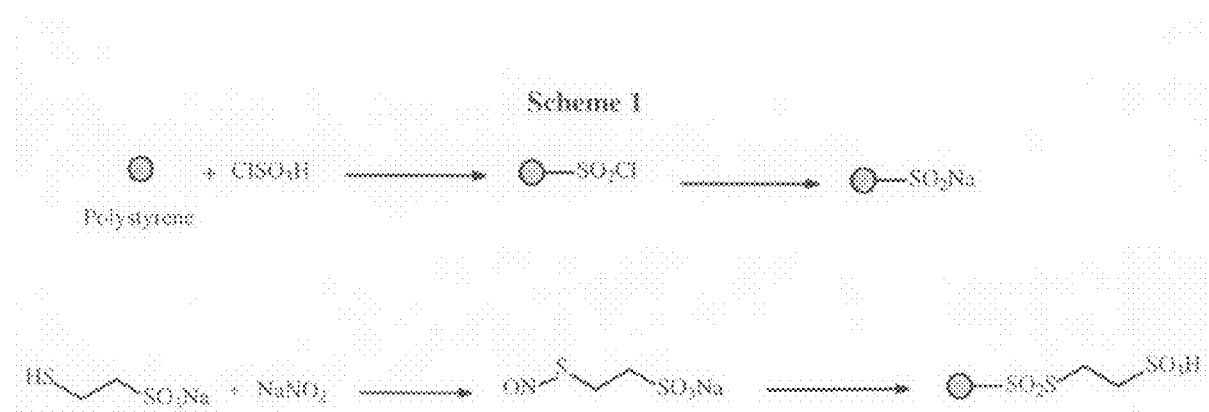
FIG. 1: Scheme 1 illustrates a preferred synthesis of the resin-bound mesna intermediates. The resin, preferably polystyrene microspheres of 200-400 mesh size, is functionalized with an appropriate linker, shown in Scheme 1 as sodium sulfinate.

Scheme 1 in FIG. 1, illustrates a preferred synthesis of the resin-bound mesna intermediates. The resin, preferably polystyrene microspheres of 200-400 mesh size, is functionalized with an appropriate linker, shown in Scheme 1 as sodium sulfinate. The functionalization of the resin is preferably carried out in a two-step process as shown. First, the resin is combined with a halogenated reactant to form an intermediate sulfinyl chloride linked resin, then a substitution reaction forms the sulfinate-linked resin.

2-mercaptoethane sulfonate sodium is then functionalized with an appropriate leaving group, preferably a nitric oxide moiety, and then reacted with the functionalized polystyrene to form the intermediate polymer bound mesna.

Figure 2:
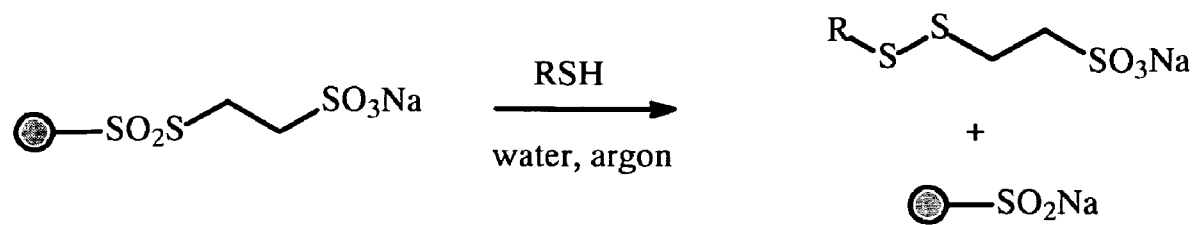
FIG. 2: Scheme 2 illustrates the synthesis of the Formula I compounds of this invention where $R_1$ is ethyl and $R_2$ is sulfonate. As shown, the synthetic process is a one-step, single pot process in which the polymer bound mesna is reacted with a sulfur-containing amino acid, preferably cysteine, homocysteine or glutathione; or by a short-chain peptide having 2-10 amino acids, at least one of which is a sulfur-containing amino acid.

Scheme 2 in FIG. 2, illustrates the synthesis of the Formula I compounds of this invention where $R_1$ is ethyl and $R_2$ is sulfonate. As shown, the synthetic process is a one-step, single pot process in which the polymer bound mesna is reacted with a sulfur-containing amino acid, preferably cysteine, homocysteine or glutathione; or by a short-chain peptide having 2-10 amino acids, at least one of which is a sulfur-containing amino acid. Configuration of the reactant amino acid(s) may be pure L-enantiomer, pure D-enantiomer, or a racemic mixture of the D and L stereoisomers.

After separation of the resin by conventional methods, virtually pure Formula I compound is obtained in high yields. The polymer bound sulfinate can be used again in the same or similar reactions.

Preferred compounds of Formula I include those compounds where X is selected from the group consisting of: cysteine (cys); homocysteine (h-cys); glutathione (GSH); glutamic acid (glu); and short-chain peptides including cyteinyl glycine (cys-gly); glycinyl cysteine (gly-cys); glucys; cys-glu; glu-gly; and gly-glu. As stated above, the optical configuration of the amino acids can be the levorotatory (L) configuration, the dextrorotatory (D) configuration, or a racemic mixture thereof. Most preferred is the more active, naturally-occurring L-isomer in each case. Detailed examples of the synthesis of certain Formula I compounds are set forth below.

The invention also includes pharmaceutical formulations that comprise a Formula I compound and one or more pharmaceutically acceptable solvents, excipients, diluents, fillers or additives, to construct a pharmaceutically elegant formulation suitable for administration to mammalian patients.

The compounds of the present invention are preferably formulated prior to administration. Therefore, another aspect of the present invention is a pharmaceutical formulation comprising a compound of Formula I and a pharmaceutically acceptable carrier, diluent, or excipient. The present pharmaceutical formulations are prepared by known procedures using well-known and readily available ingredients. In making the compositions of the present invention, the active ingredient will usually be mixed with a carrier; or dissolved or suspended in a solvent; or enclosed within a carrier, which may be in the form of a capsule, sachet, paper, or other container. The compositions can be in the form of tablets, pills, powders, lozenges, sachets, cachets, elixirs, suspensions, emulsions, solutions, syrups, aerosols, ointments containing, for example up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone (PVP), dimethylacetamide (DMA), dimethylisosorbide (DMI), N-methylpyrrolidinone (NMP), cellulose, water syrup, methyl cellulose, methyl and propyl hydroxybenzoates, talc, magnesium stearate and mineral oil. The formulations can additionally include lubricating agents, wetting agents, emulsifying and suspending agents, preserving agents, sweetening agents, or flavoring agents. Compositions of the inventions may be formulated so as to provide quick, sustained, or delayed release of the active ingredient after administration to the patient by employing procedures well known in the art.

The compositions are preferably formulated in a unit dosage form, each dosage containing from about 5 mg to about 50,000 mg, more preferably about 25 to about 30,000 mg of the active ingredient. The most preferred unit dosage form contains about 10,000 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier. The following formulation examples are illustrative only and are not intended to limit the scope of the invention in any way.

Formulation 1

Hard gelatin capsules are prepared using the following ingredients:

| Ingredient | Amount |
| --- | --- |
| Active Ingredient | 1000 mg |
| Dried Starch | 800 mg |
| Magnesium Stearate | 20 mg |

Formulation 2

A tablet is prepared using the following ingredients:

| Ingredient | Amount |
| --- | --- |
| Active Ingredient | 1000 mg |
| Microcrystalline Cellulose | 600 mg |
| Silicon Dioxide, Fumed | 10 mg |
| Stearic Acid | 10 mg |

The components are blended and compressed to form tablets.

Formulation 3

Tablets each containing Formula I compound as an active ingredient are made as follows:

| Ingredient | Amount |
| --- | --- |
| Active Ingredient | 1000 mg |
| Starch | 600 mg |
| Microcrystalline Cellulose | 300 mg |
| PVP | 2 mg |
| Magnesium Stearate | 2 mg |

The active ingredient, starch and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed utilizing a tablet machine to yield tablets each weighing approximately 2 g.

Formulation 4

Suspensions each containing 4,000 mg of medicament per 80 mL dose are made as follows:

| Ingredient | Amount |
| --- | --- |
| Active Ingredient | 4,000 mg |
| Distilled Water | 80 mL |
| Syrup | 3 mL |
| Benzoic Acid Solution | 1.0 mL |
| Artificial Flavor | q.v. |
| Artificial Color | q.v. |
| Sodium Carboxymethyl Cellulose | 400 mg |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 5

An intravenous formulation may be prepared as follows:

| Ingredient | Amount |
| --- | --- |
| Active Ingredient | 10 g |
| Purified Water | 250 mL |
| Mannitol | 100 mg |
| 1 N Sodium Hydroxide | 1 mL |

The following examples illustrate one preferred synthesis of some of the Formula I compounds. These examples are disclosed for illustrative purposes only, and are not to be construed as limiting the scope of the invention in any way.

Example 1

Preparation Of Resin Bound Mesna Intermediate From Sodium 2-Mercaptoethane Sulfonate

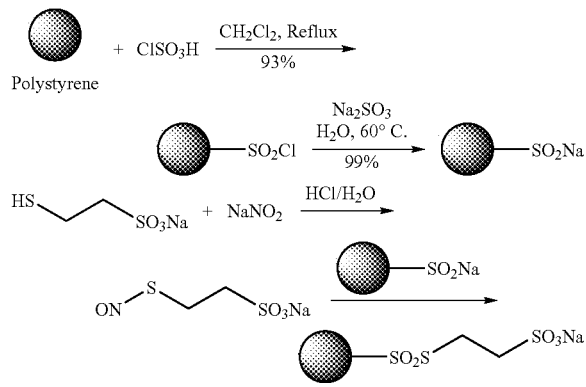

A mixture of polystyrene resin (5.0 g, Fluka, 200-400 mesh; 1% divinylbenzene) and chlorosulfonic acid (100 g) in 300 mL dichloromethane was stirred at room temperature under argon for approximately four hours, and then heated to reflux overnight. The resin was isolated by filtration while the reaction was allowed to cool to room temperature. Once the reaction temperature had cooled to room temperature, it was washed with dichloromethane (100 mL), acetonitrile (100 mL), and cold water (200 mL) sequentially. The pale brown-colored resin was then dried under high vacuum to give 9.04 g poly(styrene p-sulfonyl chloride) with 93% yield.

Poly(styrene p-sulfonyl chloride) resin (9.04 g) was suspended in 200 mL aqueous solution of sodium sulfite (60 g) and stirred at 60° C. for approximately 24 hours, isolated by filtration, washed with 200 mL water, and dried to give 8.4 gram product of mono sodium, polystyrene p-sulfinate with 99% yield.

To a solution of hydrochloric acid (2 N, 40 mL) bubbled with argon was added sodium 2-mercaptoethane sulfonate (6.56 g). The reaction solution was cooled to 0° C. in an ice bath. 20 mL aqueous solution of sodium nitrite (2.76 g) was added slowly. The reaction solution turned red and was stirred for approximately 40 minutes after the addition. The mono sodium, polystyrene p-sulfinate (3.8 g) was added and the mixture was stirred at room temperature for approximately 16 hours. The resulting polystyrene p-sulfinate bound 2-mercaptoethane sulfonic acid sodium salt was isolated by filtration, rinsed with water and dried to give 3.9 g of the title intermediate.

Example 2

L-Cysteine-Mesna Disulfide

L-Cysteine (0.50 g, 4.1 mmol) was dissolved in 50 mL de-ionized water bubbled with argon. Excessive polystyrene p-sulfinate bound 2-mercaptoethane sulfonic acid sodium salt (about 17 fold) was added. The reaction mixture was stirred under argon for approximately 4 days until all starting material of L-cysteine was consumed. The resin was removed by filtration and was recycled to prepare more disulfides. The pH of the filtrate was adjusted to neutral and lyophilized to give 0.842 g L-Cysteine-Mesna disulfide, with 72% yield.

$^1$H NMR ($D_2O$, 300 MHz) δ 3.05-3.14 (m, 3H), 3.27-3.35 (m, 3H), 3.97-4.01 (dd, 1H, J=8.1 & 4.2 Hz).

$^{13}$C NMR ($D_2O$, 75 MHz) δ 31.5, 39.0, 50.4, 53.8, 174.4.

HRMS Calcd. for $C_5H_{10}NO_5S_3$ $Na_2$ (M+Na): 305.9516; Found: 305.9495.

Example 3

DL-Homocysteine-Mesna Disulfide

DL-Cysteine (0.42 g, 3.1 mmol) was dissolved in 25 mL de-ionized water bubbled with argon. Excessive polystyrene p-sulfinate bound 2-mercaptoethane sulfonic acid sodium salt (about 8.5 fold) was added. The reaction mixture was stirred under argon for approximately 4 days until all starting material of DL-Homocysteine was consumed. The resin was removed by filtration and was recycled to prepare more disulfides. The pH of filtrate was adjusted to neutral and lyophilized. The lyophilized wet cake was then recrystallized from minimum required quantity of water to give 0.293 g (32%) DL-Homocysteine-Mesna disulfide $^1$H NMR ($D_2O$, 300 MHz) δ 2.27-2.43 (m, 2H), 2.85-2.9 (m, 2H), 3.01-3.07 (m, 2H), 3.26-3.31 (m, 2H), 4.11 (t, 1H, J=6.3 Hz,).

$^{13}$C NMR ($D_2O$, 75 MHz) δ 29.4, 31.7, 32.5, 50.4, 52.1, 172.4.

HRMS Calcd. for $C_6H_{14}NO_5S_3$ (M-$Na^+$ 2H): 276.0034; Found: 276.0029.

Example 4

Glutathione-Mesna Disulfide

Glutathione (0.54 g, 1.76 mmol) was dissolved in 25 mL de-ionized water bubbled with argon. Excessive polystyrene p-sulfinate bound 2-mercaptoethane sulfonic acid sodium salt (about 15 fold) was added. The reaction mixture was stirred under argon for 4 approximately days until all starting material of glutathione was consumed. The resin was removed by filtration and was recycled to prepare more disulfides. The pH of filtrate was adjusted to neutral and lyophilized to give 486 mg Glutathione-Mesna disulfide, with 59% yield.

$^1$H NMR ($D_2O$, 300 MHz) δ 2.07-2.14 (m, 2H), 2.47-2.54 (m, 2H), 2.94-3.08 (m, 3H), 3.25-3.32 (m, 3H), 3.66-3.71 (m, 1H), 3.75 (d, 2H, J=3.3 Hz), 4.71 (m, 1H).

$^{13}$C NMR ($D_2O$, 75 MHz) δ 26.6, 31.4, 31.9 and 32.0, 38.8, 43.6, 50.6, 52.6 and 52.8, 54.3, 172.0, 174.9, 175.2, 176.5.

HRMS Calcd for $C_{12}H_{22}N_3O_9S_3$ (M-$Na^+$ 2H): 448.0518; Found: 448.0497.

Example 5

Cysteinyl Glycine-Mesna Disulfide

Cysteinyl glycine (226 mg, 1.27 mmol) was dissolved in 25 mL de-ionized water bubbled with argon. Excessive polystyrene p-sulfinate bound 2-mercaptoethane sulfonic acid sodium salt (about 20.5 fold) was added. The reaction mixture was stirred under argon for approximately 3 days until all starting material of cysteinyl glycine was consumed. The resin was removed by filtration and was recycled to prepare more disulfides. The pH of the filtrate was adjusted to neutral and lyophilized to give 302 mg cysteinyl glycine-Mesna disulfide, with 70% yield.

$^1$H NMR (D$_2$O, 300 MHz) δ 3.07-3.19 (m, 3H), 3.27-3.39 (m, 3H), 3.93-4.1 (m, 2H), 4.41 (dd, 1H, J=8.1, 5.4 Hz).
$^{13}$C NMR (D$_2$O, 75 MHz) δ 31.8, 37.9, 43.7, 50.4, 52.4, 168.5, 176.2.

Example 6

γ-Glutamylcysteine-Mesna Disulfide

γ-Glutamyl cysteine (200 mg, 0.8 mmol) was dissolved in 25 mL de-ionized water bubbled with argon. Excessive polystyrene p-sulfinate bound 2-mercaptoethane sulfonic acid sodium salt (about 32 fold) was added. The reaction mixture was stirred under argon for approximately 3 days until all starting material of γ-Glutamyl cysteine was consumed. The resin was removed by filtration and was recycled to prepare more disulfides. The pH of the filtrate was adjusted to neutral and lyophilized to give 316 mg γ-Glutamyl cysteine-Mesna disulfide, with 96% yield.
$^1$H NMR (D$_2$O, 300 MHz) δ 2.1-2.2 (m, 2H), 2.47-2.53 (m, 2H), 2.95-3.08 (m, 3H), 3.22-3.3 (m, 3H), 3.76 (t, J=6.3 Hz, 1H), 4.47 (dd, J=9.0 & 4.2 Hz, 1H).
$^{13}$C NMR (D$_2$O, 75 MHz) δ 31.9, 39.8, 44.0, 46.4, 50.5, 54.3, 54.8, 174.6, 177.0.

The present invention also includes methods of using the Formula I compounds, and formulations that include the Formula I compounds. Potential uses include, but are not limited to reducing toxicity of antineoplastic and other toxic pharmaceuticals; reducing the toxicity of toxic industrial, agricultural or military chemicals; reducing toxicity of acute or chronic exposure to radiation; treatment or mitigation of symptoms of a number of diseases, including diabetic complications, inflammatory arthritis, inflammatory bowel disease, septic shock, ARDS and others.

Particular methods of use include administering an effective amount of the Formula I compound (or a formulation thereof) to a patient in need of treatment, or as prophylactic measures to patients in danger of exposure to one of the stated conditions. An effective amount for purposes of this application means that amount necessary to achieve the desired result. Since the Formula I compounds are of extremely low toxicity, large amounts (>40 g) can be administered safely with little or no adverse effects. Dosage may be on a single dose basis, or may be carried out on a regular schedule, depending upon the needs of the patient.

All patents, publications, scientific articles, web sites, and the like, as well as other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicant reserves the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicant reserves the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in the written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The present invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y". The letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and Applicant reserves the right to revise the application or claims to refer specifically to any individual member or any subgroup of members of the Markush group.

Other embodiments are within the following claims. The patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A compound to reduce the toxicity of a chemotherapeutic agent, wherein said compound is X—S—S—$R_1$-$R_2$ wherein:

X—S is Cysteinyl glycine $R_1$ is —$(CH_2)_2$— and $R_2$ is —$SO_3^-$ or —$P(O)(OH)_2$; or a pharmaceutically acceptable salt thereof.

* * * * *